(12) United States Patent
Nukui et al.

(10) Patent No.: US 6,944,258 B2
(45) Date of Patent: Sep. 13, 2005

(54) BEAM HARDENING POST-PROCESSING METHOD AND X-RAY CT APPARATUS

(75) Inventors: Masatake Nukui, Tokyo (JP); Shunichiro Tanigawa, Tokyo (JP)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 107 days.

(21) Appl. No.: 10/717,382

(22) Filed: Nov. 19, 2003

(65) Prior Publication Data

US 2004/0109528 A1 Jun. 10, 2004

(30) Foreign Application Priority Data

Dec. 2, 2002 (JP) ...................................... 2002-349426

(51) Int. Cl.$^7$ ................................................. A61B 6/03
(52) U.S. Cl. .............................. 378/4; 378/19; 378/901
(58) Field of Search ........................... 378/4, 8, 15, 19, 378/901

(56) References Cited

U.S. PATENT DOCUMENTS

| | | | |
|---|---|---|---|
| 4,962,514 A | 10/1990 | Hart et al. | |
| 5,528,644 A | 6/1996 | Ogawa et al. | |
| 5,953,444 A | 9/1999 | Joseph et al. | |
| 6,438,197 B2 | 8/2002 | Stierstorfer | |
| 6,470,206 B2 | 10/2002 | Nukui et al. | |
| 6,600,801 B2 | 7/2003 | Raupach | |
| 2004/0022364 A1 * | 2/2004 | Stierstorfer et al. | 378/207 |
| 2004/0196960 A1 * | 10/2004 | Tanigawa et al. | 378/207 |
| 2004/0208290 A1 * | 10/2004 | Nukui et al. | 378/207 |

FOREIGN PATENT DOCUMENTS

JP         05-130987         5/1993

* cited by examiner

*Primary Examiner*—David V Bruce
(74) *Attorney, Agent, or Firm*—Carl B. Horton, Esq.; Armstrong Teasdale LLP

(57) ABSTRACT

A beam hardening post-processing method that can improve the accuracy of channel-by-channel correction on a BH effect easily and yet taking a non-linear effect into account, phantoms of different diameters are disposed at a position offset from an imaging center to acquire projection information having a transmission length of an X-ray beam varying from view to view, hence, acquire projection information having a projection information value varying from view to view, for each channel, correction factors are determined, and a corrective function containing even a non-linear effect is determined by higher-order function fitting from the correction factors; and therefore, correction with high accuracy can be achieved in the channel-by-channel correction on the projection information values conducted after BH correction, and moreover, correction with high accuracy can be achieved using a smaller amount of phantom projection information, thus reducing the time for calibration work.

16 Claims, 10 Drawing Sheets

BEAM HARDENING POST-PROCESSING METHOD AND X-RAY CT APPARATUS

CROSS REFERENCE TO RELATED APPLICATIONS

This application claims the benefit of Japanese Application No. 2002-349426 filed Dec. 2, 2002.

BACKGROUND OF THE INVENTION

The present invention relates to a beam hardening (sometimes abbreviated as 'BH' hereinbelow) post-processing method and an X-ray CT apparatus for correcting intensity of X-rays passing through a subject based on phantom data.

An X-ray source employed in an X-ray CT apparatus outputs X-rays having a certain range of energy. On the other hand, the linear absorption coefficient for X-rays passing through a subject depends upon the X-ray energy, and exhibits a beam hardening effect by which the average energy shifts to a higher level as the transmission length through the subject becomes larger. Thus, the X-ray transmission intensity, i.e., projection information value, and the transmission length do not maintain a proportional relationship with each other, i.e., are non-linearly related to each other.

The BH effect results in a cupping effect by which intensity decreases in the central portion of a reconstructed image, and is corrected by, for example, determining a corrective function for each channel of an X-ray detector for correcting the projection information values to produce a reconstructed image with homogeneous intensity (see Patent Document 1, for example).

Moreover, to achieve correction with higher accuracy, a plurality of cylindrical phantoms of different diameters, which diameters are sufficient to generally cover the entire FOV (i.e., imaged region), disposed at an imaging center are imaged, and projection information of the phantoms are used to improve the accuracy of the aforementioned correction.

Patent Document 1

Japanese Patent Application Laid Open No. H5-130987 (pages 2–3, FIGS. 1–2).

According to the conventional technique, however, a plurality of large and difficult-to-handle phantoms must be repeatedly imaged when acquiring projection information, which takes a long time; and at the same time, it is not possible to conduct correction with high accuracy in which a non-linear effect is factored into the projection information values. Specifically, since projection information value correction with high accuracy requires a large number of projection information values having different magnitudes for every channel, phantoms having a variety of diameters disposed at the imaging center must be imaged.

Especially in acquiring calibration information for the X-ray CT apparatus, it is necessary to use two or three phantoms having diameters of 20–50 cm and conduct imaging that takes over 100 minutes only for improving the accuracy of the correction, which imposes heavy work on the operator.

In consideration of such problems, it is important to find a way to implement a beam hardening post-processing method and an X-ray CT apparatus that can improve the accuracy of channel-by-channel correction on the BH effect easily and yet taking the non-linear effect into account.

SUMMARY OF THE INVENTION

Therefore, an object of the present invention is to provide a beam hardening post-processing method and an X-ray CT apparatus that can improve the accuracy of channel-by-channel correction on the BH effect easily and yet taking the non-linear effect into account.

To solve the aforementioned problems and attain said object, a beam hardening post-processing method, in accordance with the invention of a first aspect, is characterized in comprising: obtaining one sinogram by acquiring first projection information of a phantom disposed at a position offset from an imaging center of an imaged region by imaging said phantom in a plurality of views from multiple directions; generating second projection information by performing beam hardening effect correction on said first projection information; generating third projection information by performing first function fitting on said second projection information; performing second function fitting on values. of said third projection information using values of said second projection information in all said views as an independent variable for each channel constituting said second projection information; and correcting projection information of a subject disposed in said imaged region using a corrective function determined by said second function fitting.

According to the invention of the first aspect, one sinogram is obtained by acquiring first projection information of a phantom disposed at a position offset from an imaging center of an imaged region by imaging the phantom in a plurality of views from multiple directions, second projection information is generated by performing beam hardening effect correction on the first projection information, third projection information is generated by performing first function fitting on the second projection information, second function fitting is further performed on values of the third projection information using values of the second projection information in all the views as an independent variable for each channel constituting the second projection information, and projection information of a subject disposed in the imaged region is corrected using a corrective function determined by the second function fitting; and therefore, when the corrective function is determined by the function fitting, the fitting is applied to the corrective function using a wide range of values of the second projection information because the values of the second projection information are different from view to view, and thus, the accuracy of the corrective function is improved.

A beam hardening post-processing method, in accordance with the invention of a second aspect, is characterized in comprising: obtaining a plurality of sinograms by acquiring first projection information of a plurality of phantoms having different sizes disposed at a position offset from an imaging center of an imaged region by imaging each phantom in a plurality of views from multiple directions; generating second projection information by performing beam hardening effect correction on said first projection information; generating third projection information by performing first function fitting on said second projection information; performing second function fitting on values of said third projection information using values of said second projection information in all said views and in all said sinograms as an independent variable for each channel constituting said second projection information; and correcting projection information of a subject disposed in said imaged region using a corrective function determined by said second function fitting.

According to the invention of the second aspect, a plurality of sinograms are obtained by acquiring first projection information of a plurality of phantoms having different sizes disposed at a position offset from an imaging center of an imaged region by imaging each phantom in a plurality of views from multiple directions, second projection information is generated by performing beam hardening effect correction on the first projection information, third projection information is generated by performing first function fitting on the second projection information, second function fitting is further performed on values of the third projection information using values of the second projection information in all the views and in all the sinograms as an independent variable for each channel constituting the second projection information, and projection information of a subject disposed in the imaged region is corrected using a corrective function determined by the second function fitting; and therefore, when the corrective function is determined by the second function fitting, the fitting is applied to the corrective function using a still wider range of values of the second projection information because the values of the second projection information are significantly different from sinogram to sinogram, and thus, the accuracy of the corrective function is further improved to improve image quality, or alternatively, the corrective function can be easily determined by obtaining the corrective function with high accuracy using a smaller number of phantoms.

An X-ray CT apparatus, in accordance with the invention of a third aspect, is for acquiring projection information of an X-ray beam passing through an imaged region using an X-ray detector comprising multiple channels in a plurality of views from multiple directions, and performing beam hardening effect correction on said projection information, and is characterized in comprising: obtaining means for obtaining one sinogram by acquiring first projection information of a phantom disposed at a position offset from an imaging center of said imaged region by imaging said phantom in all said views; beam hardening correcting means for generating second projection information by performing said beam hardening effect correction on said first projection information; first fitting means for generating third projection information by performing first function fitting on said second projection information; second fitting means for determining a corrective function by performing second function fitting on values of said third projection information using values of said second projection information in all said views as an independent variable for each channel constituting said second projection information; and correcting means for correcting projection information of a subject disposed in said imaged region using said corrective function.

According to the invention of a third aspect, obtaining means obtains one sinogram by acquiring first projection information of a phantom disposed at a position offset from an imaging center of an imaged region by imaging the phantom in all views, beam hardening correcting means generates second projection information by performing beam hardening effect correction on the first projection information, first fitting means generates third projection information by performing first function fitting on the second projection information, second fitting means determines a corrective function by performing second function fitting on values of the third projection information using values of the second projection information in all the views as an independent variable for each channel constituting the second projection information, and correcting means corrects projection information of a subject disposed in the imaged region using the corrective function; and therefore, when the corrective function is determined by the second function fitting, the fitting is applied to the corrective function using a wide range of values of the second projection information because the values of the second projection information are different from view to view, and thus, the accuracy of the corrective function is improved.

The X-ray CT apparatus, in accordance with the invention of a fourth aspect, is characterized in that: said phantom has a circular cross-sectional shape.

According to the invention of the fourth aspect, since the phantom has a circular cross-sectional shape, it is possible to change the value of the second projection information in a continuous manner.

The X-ray CT apparatus, in accordance with the invention of a fifth aspect, is characterized in that: said cross-sectional shape has a diameter smaller than that of said imaged region.

According to the invention of the fifth aspect, since the cross-sectional shape has a diameter smaller than that of the imaged region, work of the operator is mitigated by using a smaller phantom.

The X-ray CT apparatus, in accordance with the invention of a sixth aspect, is characterized in that: said first function fitting is performed from channel to channel of said second projection information.

According to the invention of the sixth aspect, since the first function fitting is performed from channel to channel of the second projection information, a corrective function can be determined in a channel direction.

The X-ray CT apparatus, in accordance with the invention of a seventh aspect, is characterized in that: said first function fitting is performed from view to view of one sinogram containing a plurality of series of said second projection information.

According to the invention of the seventh aspect, since the first function fitting is performed from view to view of one sinogram containing a plurality of series of the second projection information, smoothing is effected also in a view direction, and variation in the values of the second and third projection can be reduced when determining the corrective function.

The X-ray CT apparatus, in accordance with the invention of an eighth aspect, is characterized in that: said first function fitting comprises averaging means for averaging the values of said second projection information.

According to the invention of the eighth aspect, since the first function fitting averages the values of the second projection information by averaging means, smoothing can be easily achieved.

The X-ray CT apparatus, in accordance with the invention of a ninth aspect, is characterized in that: said first fitting means fits a higher-order function to the values of said second projection information.

According to the invention of the ninth aspect, since the first function fitting fits a higher-order function to the values of the second projection information, when smoothing is performed in the view direction, for example, the smoothing can be achieved by the higher-order function fitting.

The X-ray CT apparatus, in accordance with the invention of a tenth aspect, is characterized in that: said obtaining means obtains a plurality of said sinograms using a plurality of said phantoms having different diameters.

According to the invention of the tenth aspect, since the obtaining means obtains a plurality of sinograms using a plurality of phantoms having different diameters, when the corrective function is determined by the function fitting, the fitting is applied to the corrective function using a still wider range of values of the second projection information because the values of the second projection information are significantly different from sinogram to sinogram, and thus, the accuracy of the corrective function is further improved to improve image quality, or alternatively, the corrective function can be easily determined by obtaining the corrective function with high accuracy using a smaller number of phantoms.

The X-ray CT apparatus, in accordance with the invention of an eleventh aspect, is characterized in that: said beam hardening correcting means generates said second projection information by performing said beam hardening effect correction on said first projection information for each of said plurality of sinograms.

According to the invention of the eleventh aspect, since the beam hardening correcting means generates the second projection information by performing the beam hardening effect correction on the first projection information for each of the plurality of sinograms, the third projection information can be generated for each sinogram.

The X-ray CT apparatus, in accordance with the invention of a twelfth aspect, is characterized in that: said first function fitting generates said third projection information by performing said first function fitting on said second projection information for each of said plurality of sinograms.

According to the invention of the twelfth aspect, since the first function fitting generates the third projection information by performing the first function fitting on the second projection information for each of the plurality of sinograms, a corrective function can be determined for each sinogram.

The X-ray CT apparatus, in accordance with the invention of a thirteenth aspect, is characterized in that: said second fitting means determines said corrective function of a first order for each said sinogram.

According to the invention of the thirteenth aspect, since the second fitting means determines a first-order corrective function for each sinogram, calculation efficiency is improved by determining approximate corrective functions.

The X-ray CT apparatus, in accordance with the invention of a fourteenth aspect, is characterized in that: said second fitting means determines a higher-order corrective function by performing higher-order function fitting on said corrective functions of a first order.

According to the invention of the fourteenth aspect, since the second fitting means determines a higher-order corrective function by performing higher-order function fitting on the corrective functions of a first order, a higher-order corrective function containing a non-linear effect can be easily determined.

The X-ray CT apparatus, in accordance with the invention of a fifteenth aspect, is characterized in that: said second fitting means determines the corrective function by performing function fitting on the values of said third projection information for all said sinograms.

According to the invention of the fifteenth aspect, since the second fitting means determines the corrective function by performing function fitting on the values of the third projection information for all the sinograms, a corrective function with high accuracy can be determined from a large amount of the second and third projection information.

The X-ray CT apparatus, in accordance with the invention of a sixteenth aspect, is characterized in that: said corrective function contains higher-order terms.

According to the invention of the sixteenth aspect, since the corrective function contains higher-order terms, a non-linear effect can be included to achieve fitting with high accuracy According to the present invention, obtaining means obtains one sinogram or a plurality of sinograms by acquiring first projection information of a phantom or a plurality of phantoms of different diameters disposed at a position offset from an imaging center of an imaged region by imaging each phantom in all views, beam hardening correcting means generates second projection information by performing beam hardening effect correction on the first projection information, first fitting means generates third projection information by performing first function fitting on the second projection information, second fitting means determines a corrective function by performing second function fitting on values of the third projection information using values of the second projection information in all the views as an independent variable for each channel constituting the second projection information, and correcting means corrects projection information of a subject disposed in the imaged region using the corrective function; and therefore, when the corrective function is determined by the function fitting, the fitting is applied to the corrective function using a wide range of values of the second projection information because the values of the second projection information are different from view to view or from sinogram to sinogram, and thus, the accuracy of the corrective function is improved to improve image quality, or alternatively, the corrective function can be easily determined by obtaining the corrective function with high accuracy using a smaller number of phantoms.

Further objects and advantages of the present invention will be apparent from the following description of the preferred embodiments of the invention as illustrated in the accompanying drawings.

DETAILED DESCRIPTION OF THE INVENTION

Preferred embodiments of a beam hardening post-processing method and an X-ray CT apparatus in accordance with the present invention will now be described with reference to the accompanying drawings.

Figure 1:
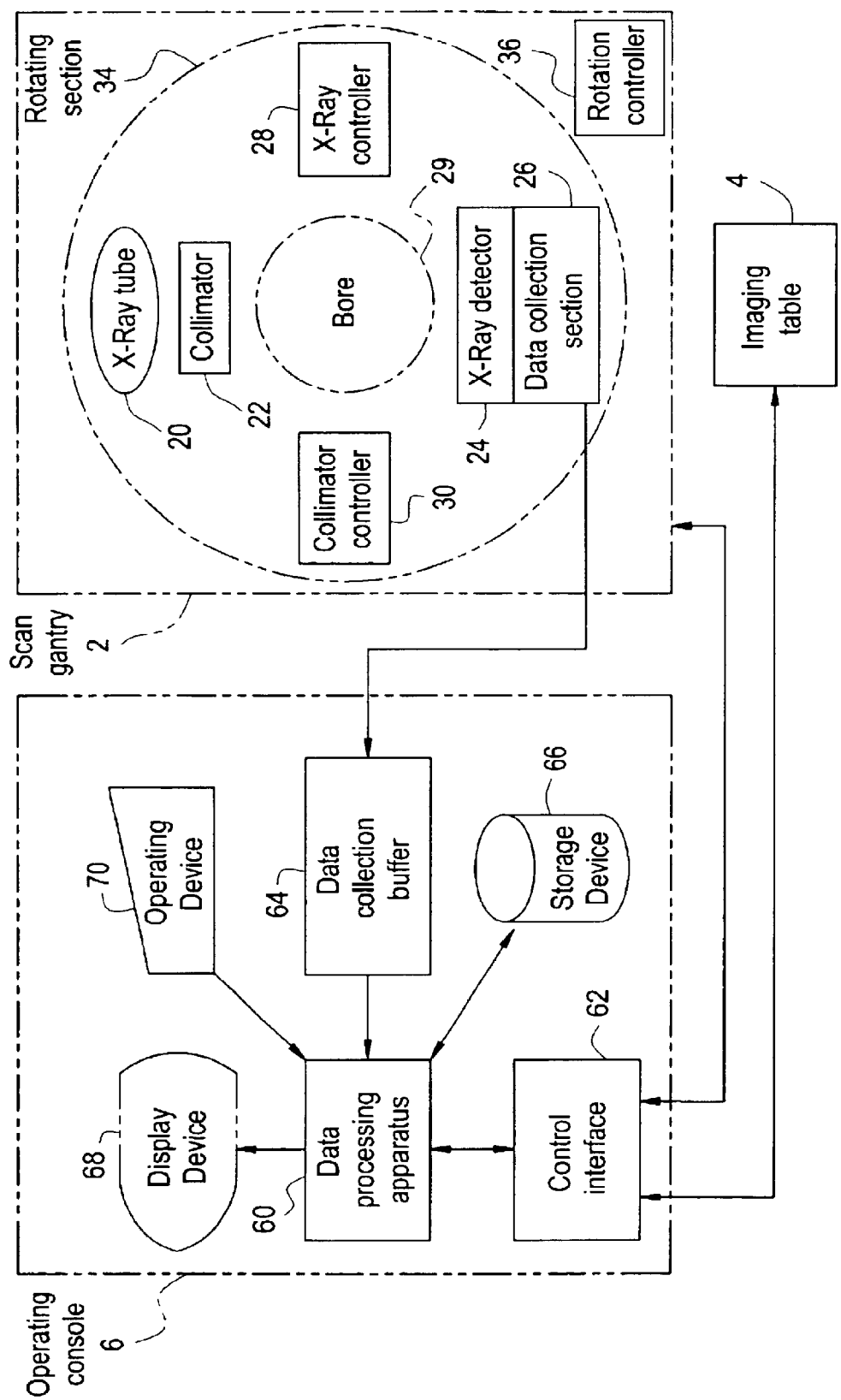
FIG. 1 is a block diagram showing the general configuration of an X-ray CT apparatus.

The general configuration of the X-ray CT apparatus of the present embodiment will be first described. FIG. 1 shows a block diagram of an X-ray CT apparatus. As shown in FIG. 1, the apparatus comprises a scan gantry 2 and an operating console 6.

The scan gantry 2 has an X-ray tube 20. X-rays (not shown) emitted from the X-ray tube 20 are formed into a fan-shaped X-ray beam, i.e., fan-beam X-rays, for example, by a collimator 22, and projected toward an X-ray detector 24.

The X-ray detector 24 has a plurality of X-ray detector elements arranged in line as an array in the extent direction of the fan-beam X-rays. The X-ray detector 24 is a multi-channel detector in which the plurality of X-ray detector elements are arranged in line as an array.

The X-ray detector 24 as a whole forms an X-ray impingement surface curved as a cylindrical concavity. The X-ray detector 24 is formed of a combination of scintillators and photodiodes, for example. It should be noted that the X-ray detector 24 is not limited thereto but may comprise semiconductor X-ray detector elements using cadmium telluride (CdTe) or the like, or ionization chamber X-ray detector elements using xenon (Xe) gas, for example. The X-ray tube 20, collimator 22 and X-ray detector 24 together constitute an X-ray emitting/detecting apparatus.

The X-ray detector 24 is connected with a data collecting section 26. The data collecting section 26 collects data detected by the individual detector elements in the X-ray detector 24. The emission of the X-rays from the X-ray tube 20 is controlled by an X-ray controller 28. The interconnection between the X-ray tube 20 and X-ray controller 28 and that between the collimator 22 and a collimator controller 30 are omitted in the drawing. The collimator 22 is controlled by the collimator controller 30.

The above-described components from the X-ray tube 20 through the collimator controller 30 are mounted on a rotating section 34 of the scan gantry 2. In this configuration, a subject or a phantom is laid on a cradle within a bore 29 in the center of the rotating section 34. The rotating section 34 is controlled by a rotation controller 36 to rotate, while X-rays are emitted from the X-ray tube 20 and X-rays passing through the subject or phantom are detected at the X-ray detector 24 as projection information for each view. The interconnection between the rotating section 34 and rotation controller 36 is omitted in the drawing.

The operating console 6 has a data processing apparatus 60. The data processing apparatus 60 comprises, for example, a computer. The data processing apparatus 60 is connected with a control interface 62. The control interface 62 is connected with the scan gantry 2. The data processing apparatus 60 controls the scan gantry 2 via the control interface 62.

The data collecting section 26, X-ray controller 28, collimator controller 30 and rotation controller 36 in the scan gantry 2 are controlled via the control interface 62. The individual connections between these sections and the control interface 62 are omitted in the drawing.

The data processing apparatus 60 is also connected with a data collection buffer 64. The data collection buffer 64 is connected with the data collecting section 26 in the scan gantry 2. Data collected at the data collecting section 26 are input to the data processing apparatus 60 via the data collection buffer 64.

The data processing apparatus 60 performs image reconstruction using transmitted X-ray signals, or projection information, collected via the data collection buffer 64. The data processing apparatus 60 is also connected with a storage device 66. The storage device 66 stores projection information collected in the data collection buffer 64, reconstructed tomographic image information, programs for implementing the functions of the present apparatus, and so forth.

The data processing apparatus 60 is further connected with a display device 68 and an operating device 70. The display device 68 displays the tomographic image information and other information output from the data processing apparatus 60. The operating device 70 is operated by an operator, and supplies several kinds of instructions and information to the data processing apparatus 60. The operator interactively operates the present apparatus using the display device 68 and operating device 70. The scan gantry 2, an imaging table 4 and the operating console 6 together constitute an acquiring apparatus for imaging the subject or phantom to acquire a tomographic image.

Figure 2:
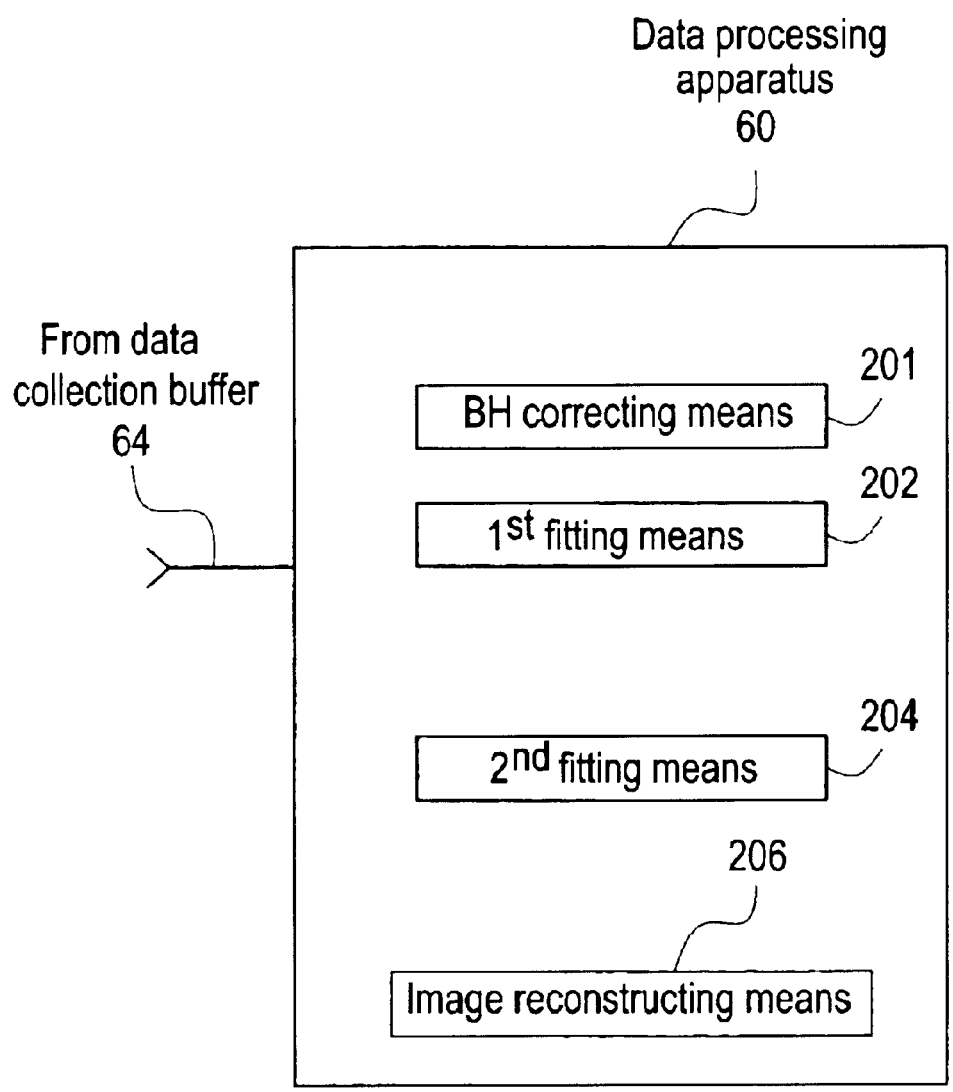
FIG. 2 is a functional block diagram showing a data processing apparatus of Embodiment 1.

FIG. 2 shows a functional block diagram of only a portion associated with the beam hardening post-processing method, which is one embodiment of the present invention, in the data processing apparatus 60. The data processing apparatus 60 comprises the functions of BH correcting means 201, first fitting means 202, second fitting means 204 and image reconstructing means 206 performed on the projection information in the storage device 66.

The BH correcting means 201 performs BH correction on the projection information in the storage device 66. Representing a value of the projection information acquired at each channel in the X-ray detector 24 as Ih, and BH corrected data as Ic, the BH correction is conducted according to the following equation:

$$Ic = B_0 \cdot Ih + B_1 \cdot Ih^2 + B_2 \cdot Ih^3 + B_3 \cdot Ih^4, \quad (1)$$

where B0–B3 are correction factors. The correction factors are established for each channel by a method described in Patent Document 1, for example, and are saved in the storage device 66 in a correction factor table.

The first fitting means 202 performs channel-to-channel or view-to-view smoothing on the projection information in the storage device 66. The first fitting means 202 conducts the fitting by averaging means for performing channel-to-channel or view-to-view average calculation, or by fitting a higher-order function to the projection information values in a channel or view direction. A function determined by the fitting offers a similar effect to that by smoothing because high frequency components beyond the order of the function are removed.

The second fitting means 204 performs first-order or higher-order function fitting on projection information values acquired by one channel in the X-ray detector 24 and subjected to the first function fitting by the first fitting means 202. Thus, a corrective function similar to Equation (1) used by the BH correcting means 201 can be obtained.

The image reconstructing means 206 reconstructs a tomographic image of the subject or phantom using a sinogram that is projection information comprised of a plurality of views in the storage device 66. The image reconstruction is conducted by using a filtered backprojection method, for example, and the reconstructed image is displayed on the display device 68.

Next, before explaining the operation of the X-ray CT apparatus in accordance with one embodiment of the present invention, data collection, projection information and a sinogram for a phantom disposed at a position offset from the imaging center of the bore 29 will be described.

Figure 3:
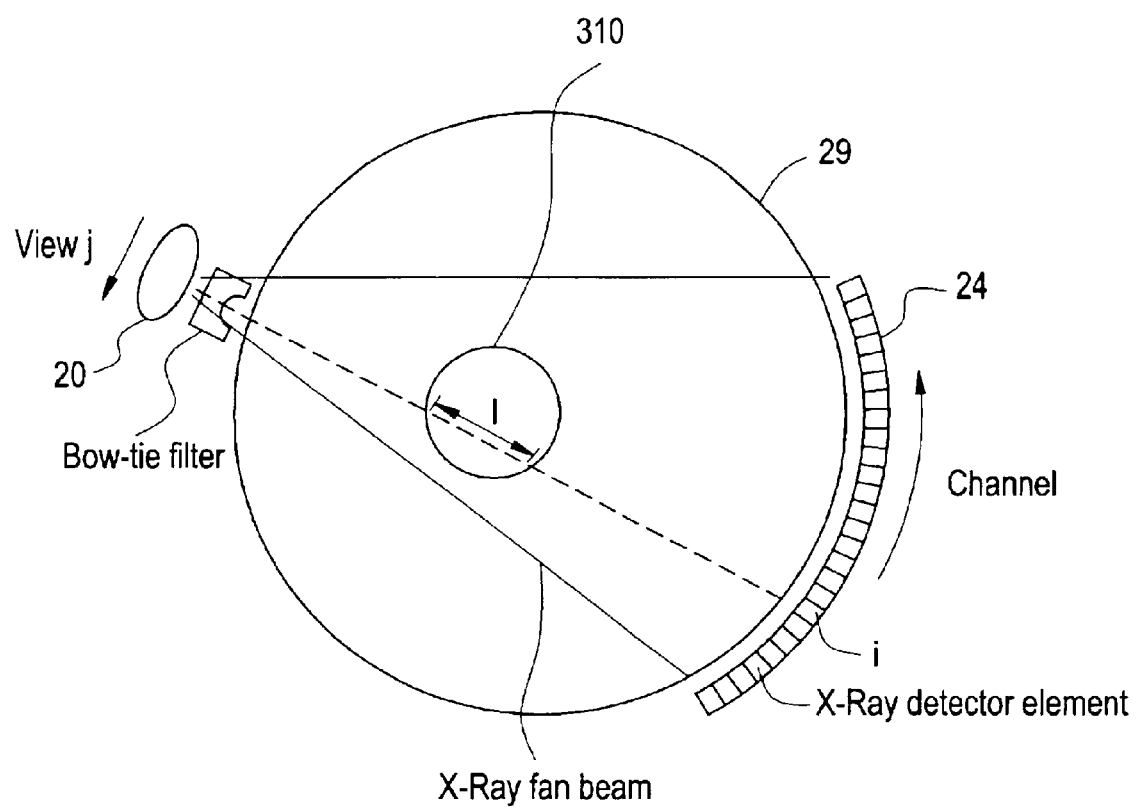
FIG. 3 shows a positional relationship between a phantom and a rotating section of Embodiment 1.

FIG. 3 shows a phantom 310 disposed in the bore 29 of the scan gantry 2. The phantom 310 has a circular cross section, and its center lies at a position different from the imaging center of the bore 29. An X-ray fan beam generated from the X-ray tube 20 and passing through a bow-tie filter passes through the phantom 310, and is detected by the X-ray detector 24.

The X-ray detector 24 in which a plurality of X-ray detector elements are arranged in line in a array in the extent direction of the X-ray fan beam detects projection information of the phantom 310 at individual channels in the array. The X-ray detector 20, collimator 22 and X-ray detector 24 are opposingly disposed with respect to the bore 29, and conducts projection information acquisition while rotating around the bore 29 along with the rotating section 34 without changing their relative positions. The projection information is acquired for each view index that corresponds to a rotation angle, and one sinogram is generated.

Figure 4A:
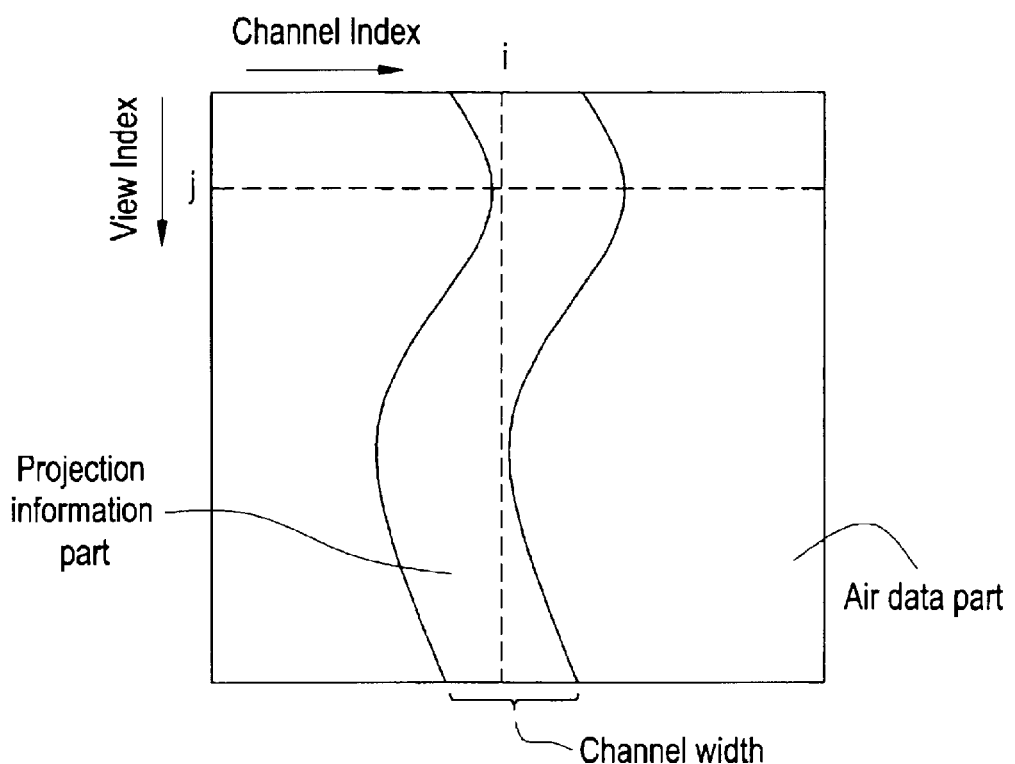
FIG. 4 shows a sinogram and projection information values of the phantom of Embodiment 1.

FIG. 4(A) shows an exemplary sinogram when the phantom 310 is used. The sinogram is comprised of a projection information part lying near the center of the channels and an air data part lying near the peripheries of the channels. Since the phantom 310 is disposed offset from the imaging center, the position of a width of channels of the projection information part varies in position with the rotation of the rotating section 34, i.e., with the varying view index, and meanders in the view index direction as shown in FIG. 4(A). For the same reason, the width of channels of the projection information part moves with the varying view index.

Figure 4B:
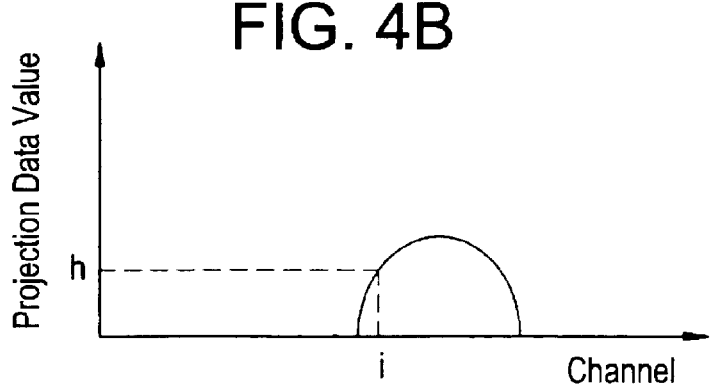

FIG. 4(B) is a diagram in which projection information at a view index of j in FIG. 4(A) is represented with a horizontal axis of the channel index and a vertical axis of the projection information value. Since the projection information value is proportional to the transmission length of the X-ray beam passing through the phantom 310, X-rays passing through near the center of the phantom 310 exhibit a higher projection information value because of a larger transmission length, and those passing through near the peripheries of the phantom 310 exhibit a lower projection information value because of a smaller transmission length, resulting in a semicircular projection image as shown in FIG. 4(B).

As an example, consider a projection information value at a view index of j and a channel index of i. An X-ray beam indicated by a broken line in FIG. 3 impinges upon the channel index i in the X-ray detector 24 when the view index is j. Define the length over which the X-ray beam passes through the phantom 310 at that time as l. The relationship of the length l to a projection information value h at the channel i in FIG. 4(B) is:

$$l \propto h.$$

Moreover, since the phantom 310 lies offset from the imaged region in FIG. 3, the transmission length l of the channel i varies from view to view. Therefore, the projection information value h of the channel i shown in FIG. 4(B) varies from view to view.

Figure 4C:
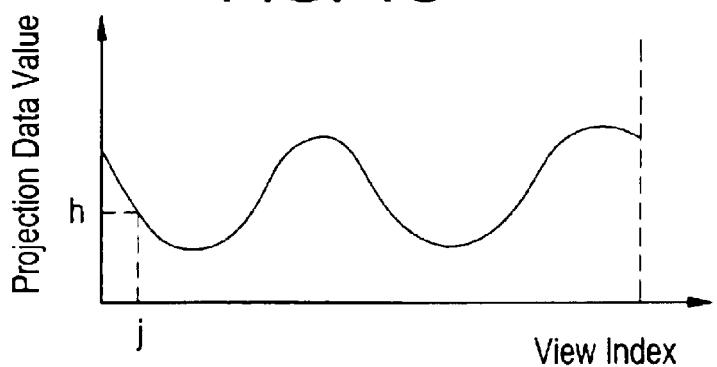

FIG. 4(C) is a diagram in which the projection information value of a channel index of i in FIG. 4(A) is represented with a horizontal axis of the view index and a vertical axis of the projection information value. Since the projection information value is proportional to the transmission length of the X-ray beam passing through the phantom 310, which length varies from view index to view index, a periodic function as shown in FIG. 4(C) results.

Figure 5:
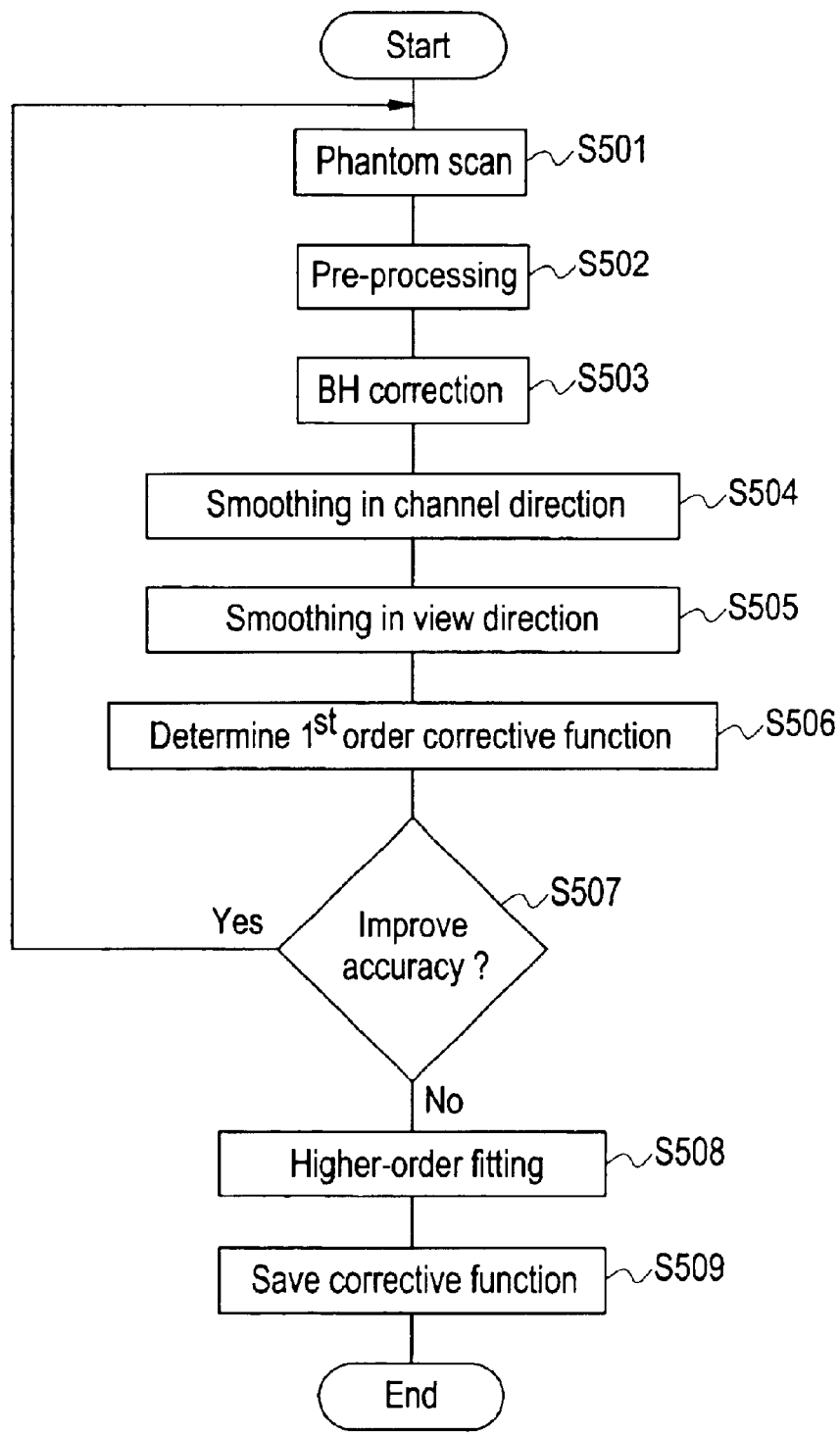
FIG. 5 is a flow chart showing the operation of the data processing apparatus of Embodiment 1.
Figure 6:
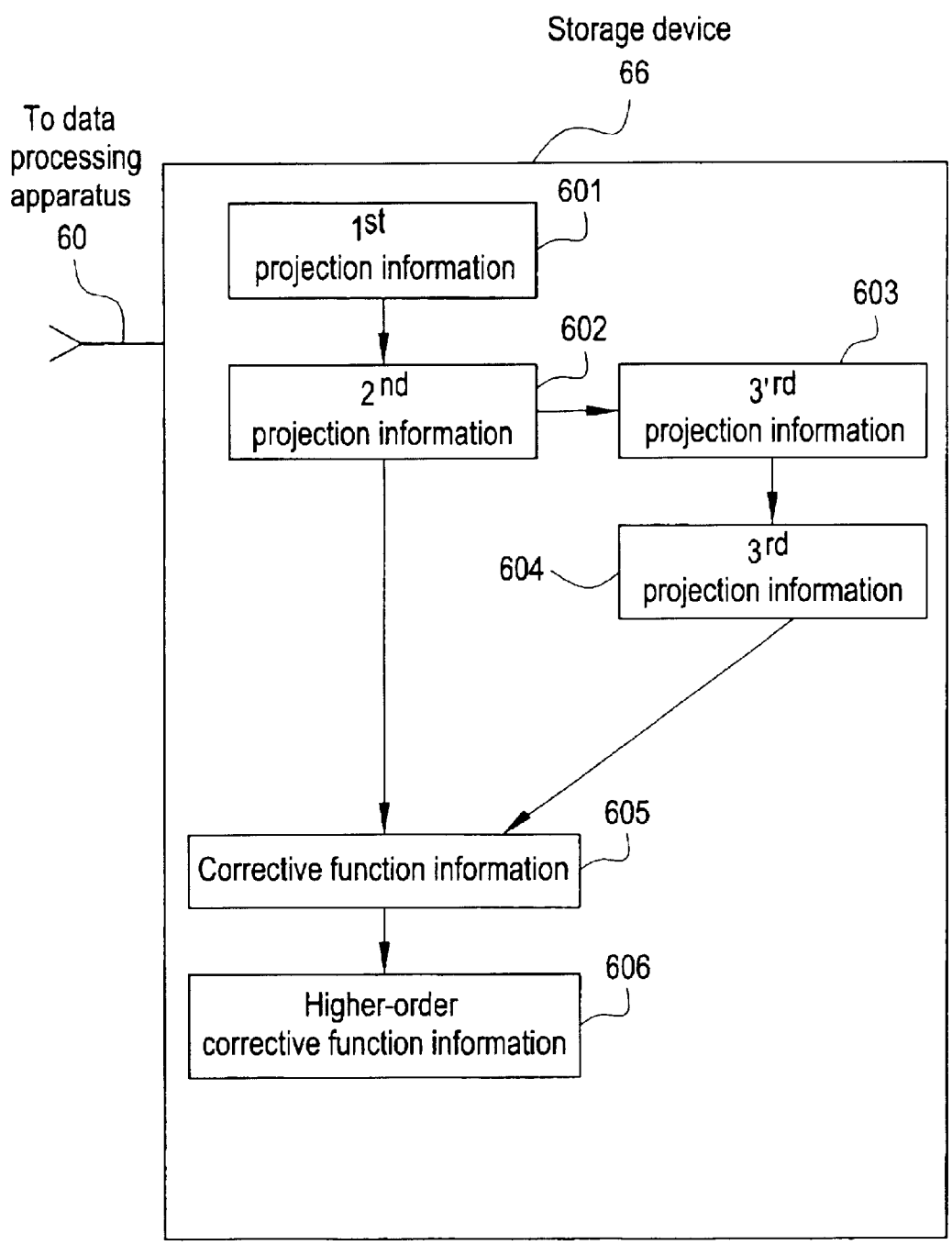
FIG. 6 is a block diagram showing files in a storage device of Embodiment 1.

Next, the operation for determining the correction factors in the BH post-processing will be described. FIG. 5 is a flow chart showing the operation for determining the correction factors in accordance with an embodiment of the present embodiment. Moreover, FIG. 6 shows files of intermediate projection information created in this operation. A phantom is first disposed at a position offset from the imaging center in the bore 29. The phantom is made from a material such as polypropylene, and has a cylindrical shape with a diameter of 35 cm, for example. The phantom is used to conduct a phantom scan (Step S501). In FIG. 6, first projection information 601 acquired by the scan is shown. A sinogram comprised of the first projection information is subjected to pre-processing such as noise removal and sensitivity correction (Step S502).

Figure 7A:
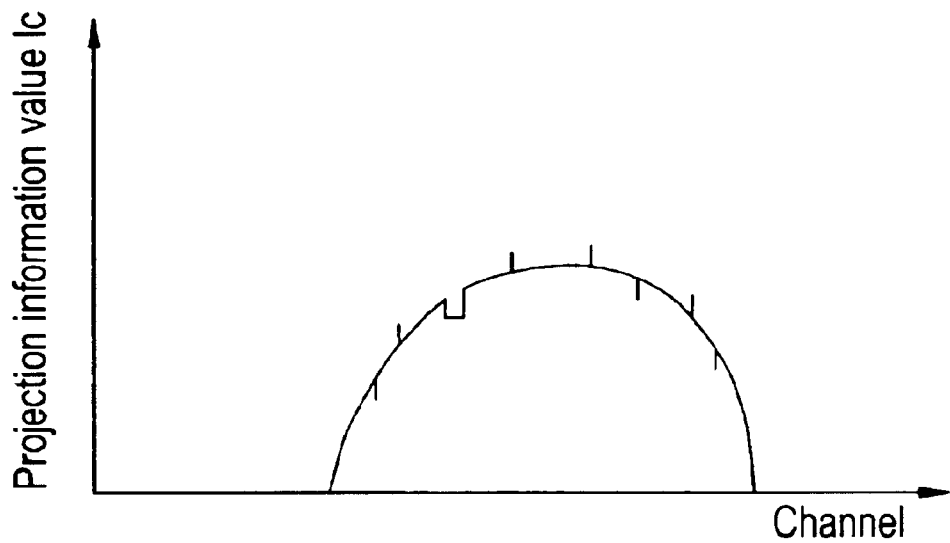
FIG. 7 shows processing on projection information values in a channel direction in accordance with one embodiment.
Figure 8A:
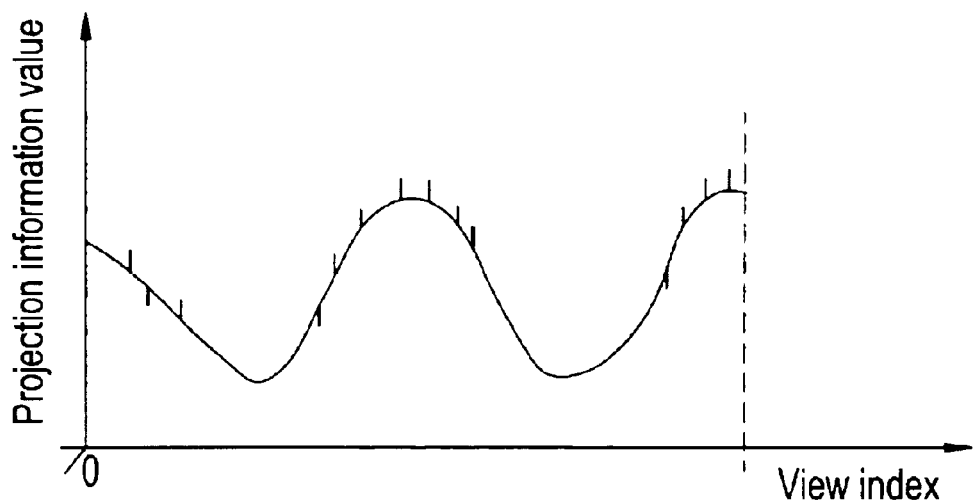
FIG. 8 shows processing on the projection information values in a view direction in accordance with the embodiment.

Then, BH correction is applied to a projection information value Ih using Equation (1) to obtain a corrected projection information value Ic (Step S503). Second projection information shown in FIG. 6 is thus generated. In this file, the BH effect is largely removed, but some BH effect due to channel-by-channel variation in the X-ray detector 24 is still left. Exemplary second projection information is schematically shown in FIG. 7(A). Although the second projection information has a generally semicircular shape that represents projection information of the circular phantom, the projection information value Ic varies in a pulse-like manner because of differences in X-ray sensitivity among some channels, for example. The variation must be corrected channel by channel because it is a phenomenon specific to individual channels. Moreover, FIG. 8(A) schematically shows exemplary projection information values in the second projection information of one channel in the view direction. The projection information value Ic varies in a pulse-like manner among some view indices.

Figure 7B:
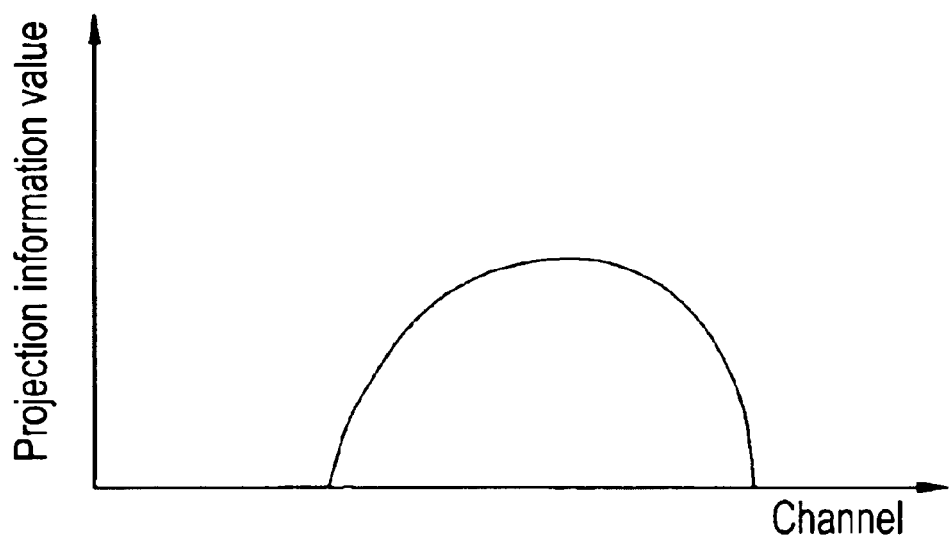

Referring again to FIG. 5, the second projection information 602 is then used to perform smoothing in the channel direction by the first fitting means 202 (Step S504). This step generates third-prime projection information 603 shown in FIG. 6. In the projection information, the projection information value Ic resulting from the channel-to-channel variation is smoothed and removed. Exemplary third-prime projection information is schematically shown in FIG. 7(B). Only the semicircular shape that represents projection information of the circular phantom is obtained as the projection information.

Figure 8B:
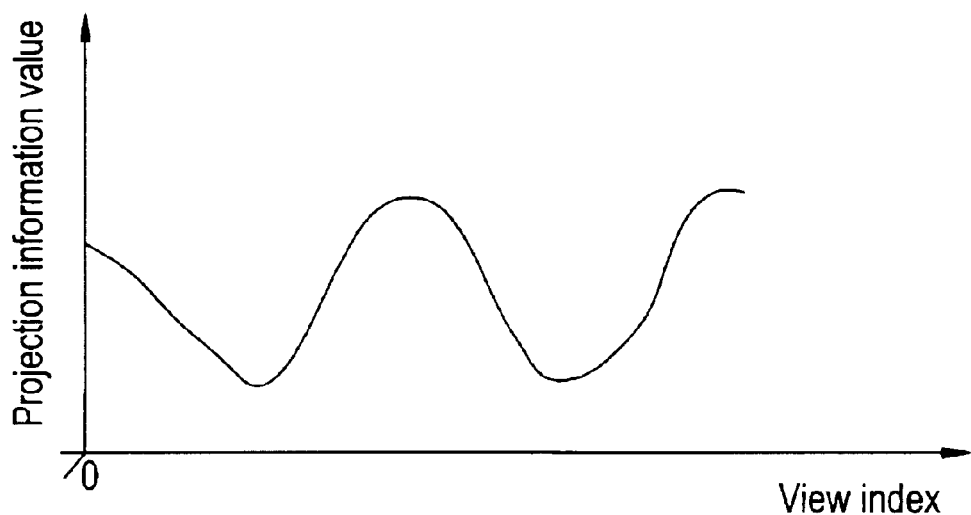

Referring again to FIG. 5, the third-prime projection information 603 is then used to perform smoothing in the view direction by the first fitting means 202 (Step S505). This step generates third projection information 604 shown in FIG. 6. In the projection information, the projection information values Ic resulting from the view-to-view variation in one channel is smoothed. Exemplary third projection information is schematically shown in FIG. 8(B). The periodic projection information values of one channel in the view direction are smoothed.

Figure 9A:
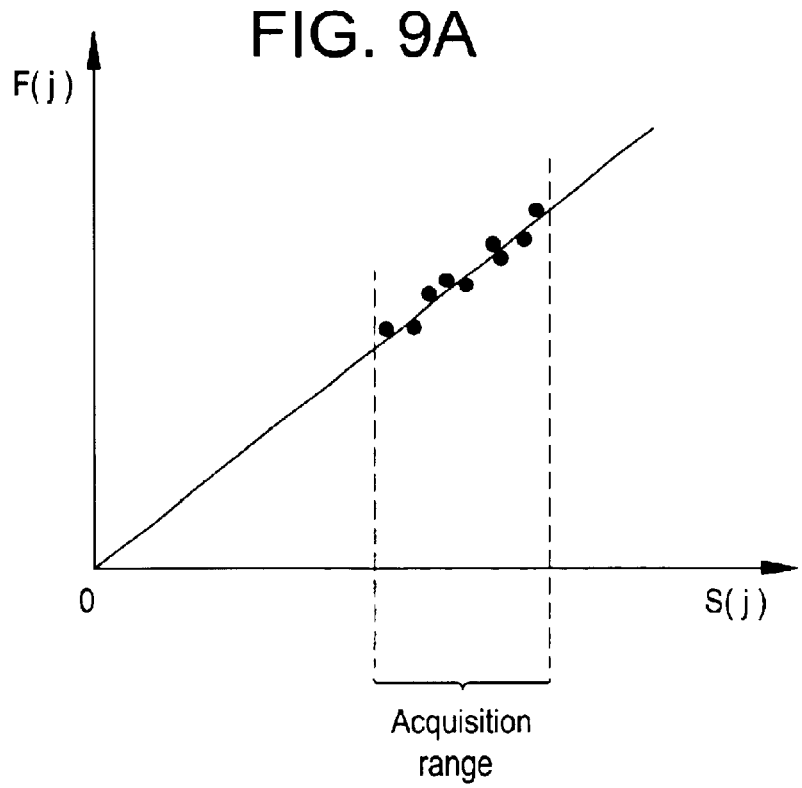
FIG. 9 shows correction factors for the projection information values in accordance with the embodiment.

Referring again to FIG. 5, a first-order corrective function is determined from the second and third projection information using the second fitting means 204 (Step S506). Representing a projection information value of the second projection information at a channel index of i as S(j), a corresponding projection information value of the third projection information as F(j), and plotting the projection information values for all view indices with a horizontal axis of S(j) and a vertical axis of F(j), the projection information values are lined up on a straight line generally passing through the origin, as shown in FIG. 9. The straight line is defined as a corrective function for the channel i. Moreover, the corrective function is saved as corrective function information 605 in the storage device 66. Representing the gradient of the corrective function as Ki, the following relationship holds:

$$F(j)/S(j)=Ki.$$

Multiplying a BH-corrected projection information value Ic of the channel i acquired from a subject by the correction factor Ki gives:

$$Ip=Ic \cdot Ki,$$

and a smoothed and corrected projection information value Ip of the subject is thus obtained.

As shown in FIG. 9, magnitude of the projection information value S(j) and the acquired value range depend upon the diameter and the position in the bore 29 of the phantom 310 because the magnitude of the projection information value is proportional to the transmission length l shown in FIG. 3.

Referring again to FIG. 5, whether or not to improve the accuracy of the corrective function is determined (Step S507). If the accuracy of the corrective function is to be improved (Yes in Step S507), a phantom of a diameter different from that of the phantom 310 is disposed at a position different from the imaging center in the bore 29, and the flow goes back to Step S501. Then, a new corrective function is obtained.

Figure 9B:
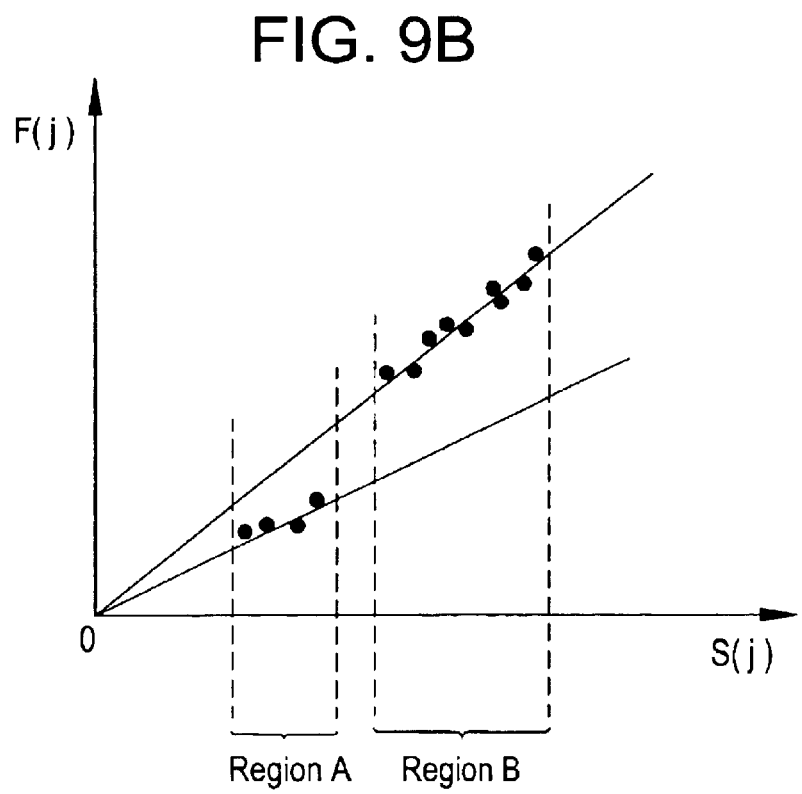

FIG. 9(B) shows exemplary corrective functions obtained by using two phantoms of different diameters. A transmission length of an X-ray beam depends upon the diameter and position of the phantom, and so does a projection information value S(j). Therefore, when the diameters of the phantoms are represented as A and B, and if A<B, the projection information values of the phantom A lie in a region A and those of the phantom B lie in a region B, as generally depicted in FIG. 9(B). The corrective functions are determined from the projection information values in these regions.

Figure 10:
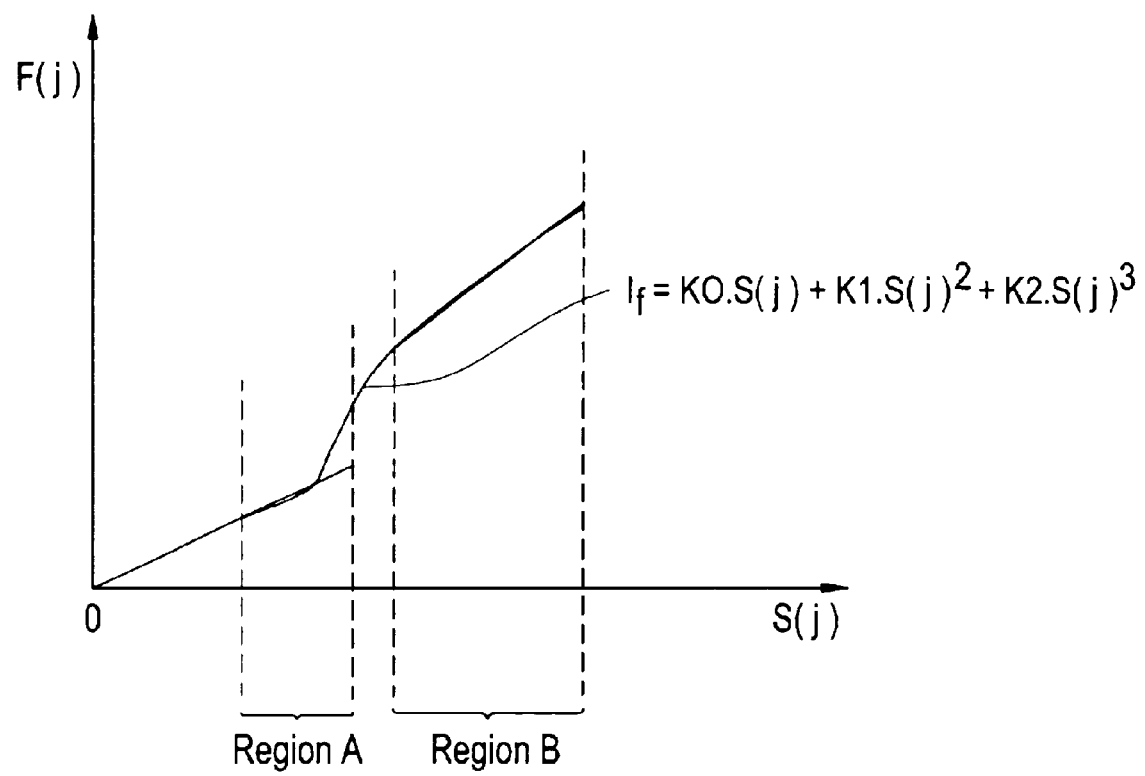
FIG. 10 is a diagram explaining determination of a second fitting function for the projection information values in accordance with the embodiment.

Thereafter, if sufficient data in view of the accuracy of the corrective function has been acquired (No in Step S507), a higher-order function fitting is applied to the correction factors in each of the acquired regions (Step S508). FIG. 10 shows a case in which the corrective functions for the phantoms A and B shown in FIG. 9(B) are employed. A third-order fitting function given below is fit to values of the corrective function A in the region A and of the corrective function B in the region B:

$$If=K0 \cdot S(j)+K1 \cdot S(j)^2+K2 \cdot S(j)^3, \qquad (2)$$

to determine the correction factors K0, K1 and K2. At that time, the correction factors in the region A having smaller projection information values may be regarded as having higher accuracy than those in the region B having larger projection information values, and therefore, it is possible to apply weighting for each region and determine the correction factors in Equation (2) so that the fitting is effected more accurately in the region A.

Referring again to FIG. 5, higher-order corrective function information 606 comprised of the correction factor values K0, K1 and K2 is then saved in the storage device 66 (Step S509), and the process is terminated.

When conducting imaging of a subject, the correction factors K0 K1 and K2 for each channel are applied to BH-corrected projection information values Ic of the subject to determine corrected projection information values If from Equation (2). The projection information values If are then subjected to image reconstruction by the image reconstructing means 206 to obtain tomographic image information.

As explained in the preceding description, in the present embodiment, since phantoms of different diameters are disposed at a position offset from the imaging center and projection information having the transmission length of the X-ray beam varying from view to view, and hence the projection information value varying from view to view, is acquired for each channel, channel-by-channel correction on the projection information values conducted after BH correction can be achieved by approximating a corrective function using a higher-order function while taking non-linear components into account, and moreover, a corrective function with high accuracy can be determined using a smaller amount of phantom data, therefore mitigating physical work and reducing the time for the work for calibration by the operator.

Moreover, although the fitting is performed using a third-order function using Equation (2) in this embodiment, the fitting may be performed using second-order or fourth- or higher-order function.

Furthermore, although a first-order corrective function is determined for each sinogram at Step S506 in the embodiment, the second projection information 602 and third projection information 604 for each sinogram are fitted with a higher-order function to determine a higher-order corrective function without determining the first-order corrective function.

Many widely different embodiments of the invention may be configured without departing from the spirit and the scope of the present invention. It should be understood that the present invention is not limited to the specific embodiments described in the specification, except as defined in the appended claims.

What is claimed is:

1. A beam hardening post-processing method comprising the steps of:

obtaining one sinogram by acquiring first projection information of a phantom disposed at a position offset from an imaging center of an imaged region by imaging said phantom in a plurality of views from multiple directions;

generating second projection information by performing beam hardening effect correction on said first projection information;

generating third projection information by performing first function fitting on said second projection information;

performing second function fitting on values of said third projection information using values of said second projection information in all said views as an independent variable for each channel constituting said second projection information; and correcting projection information of a subject disposed in said imaged region using a corrective function determined by said second function fitting.

2. A beam hardening post-processing method comprising the steps of:

obtaining a plurality of sinograms by acquiring first projection information of a plurality of phantoms having different sizes disposed at a position offset from an imaging center of an imaged region by imaging each phantom in a plurality of views from multiple directions;

generating second projection information by performing beam hardening effect correction on said first projection information;

generating third projection information by performing first function fitting on said second projection information;

performing second function fitting on values of said third projection information using values of said second projection information in all said views and in all said sinograms as an independent variable for each channel constituting said second projection information; and correcting projection information of a subject disposed in said imaged region using a corrective function determined by said second function fitting.

3. An X-ray CT apparatus for acquiring projection information of an X-ray beam passing through an imaged region using an X-ray detector comprising multiple channels in a plurality of views from multiple directions, and performing beam hardening effect correction on said projection information, comprising:

an obtaining device for obtaining one sinogram by acquiring first projection information of a phantom disposed at a position offset from an imaging center of said imaged region by imaging said phantom in all said views;

a beam hardening correcting device for generating second projection information by performing said beam hardening effect correction on said first projection information;

a first fitting device for generating third projection information by performing first function fitting on said second projection information;

a second fitting device for determining a corrective function by performing second function fitting on values of said third projection information using values of said second projection information in all said views as an independent variable for each channel constituting said second projection information; and a correcting device for correcting projection information of a subject disposed in said imaged region using said corrective function.

4. The X-ray CT apparatus of claim 3, wherein said phantom has a circular cross-sectional shape.

5. The X-ray CT apparatus of claim 4, wherein said cross-sectional shape has a diameter smaller than that of said imaged region.

6. The X-ray CT apparatus of claim 3, wherein said first function fitting is performed from channel to channel of said second projection information.

7. The X-ray CT apparatus of claim 3, wherein said first function fitting device performs said first function fitting from view to view of one sinogram containing a plurality of series of said second projection information.

8. The X-ray CT apparatus of claim 3, wherein said first function fitting device comprises averaging device for averaging the values of said second projection information.

9. The X-ray CT apparatus of claim 3, wherein said first function fitting device fits a higher-order function to the values of said second projection information.

10. The X-ray CT apparatus of claim 3, wherein said obtaining device obtains a plurality of said sinograms using a plurality of said phantoms having different diameters.

11. The X-ray CT apparatus of claim 10, wherein said beam hardening correcting device generates said second projection information by performing said beam hardening effect correction on said first projection information for each of said plurality of sinograms.

12. The X-ray CT apparatus of claim 11, wherein said first fitting device generates said third projection information by performing said first function fitting on said second projection information for each of said plurality of sinograms.

13. The X-ray CT apparatus of claim 12, wherein said second fitting device determines said corrective function of a first order for each said sinogram.

14. The X-ray CT apparatus of claim 13, wherein said second fitting device determines a higher-order corrective function by performing higher-order function fitting on said corrective functions of a first order.

15. The X-ray CT apparatus of claim 12, wherein said second fitting device determines the corrective function by performing function fitting on the values of said third projection information for all said sinograms.

16. The X-ray CT apparatus of claim 15, wherein said corrective function contains higher-order terms.

* * * * *